United States Patent
Newell et al.

(10) Patent No.: US 6,274,126 B1
(45) Date of Patent: *Aug. 14, 2001

(54) COMPOSITION FOR LIGHTENING AND HIGHLIGHTING HAIR

(75) Inventors: Gerald Newell, Hoffman Estates; Daniel Raymond Pyles, Chicago, both of IL (US)

(73) Assignee: Helene Curtis, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/138,189

(22) Filed: Aug. 21, 1998

(51) Int. Cl.$^7$ ................................. A61K 7/135
(52) U.S. Cl. .................. 424/62; 424/70.28; 424/70.12; 424/70.1
(58) Field of Search .................. 424/62, 70.1, 70.28, 424/70.12

(56) References Cited

U.S. PATENT DOCUMENTS

| | | | |
|---|---|---|---|
| 3,816,615 | * | 6/1974 | Zeffren et al. ............... 424/62 |
| 3,912,446 | * | 10/1975 | Zviak et al. ............... 8/10.1 |
| 4,096,243 | * | 6/1978 | Feinland et al. ............... 424/62 |
| 4,656,043 | * | 4/1987 | Hawkins et al. ............... 424/70 |
| 4,749,565 | * | 6/1988 | Grollier ............... 424/70 |
| 4,925,666 | * | 5/1990 | Decker, Jr. et al. ............... 424/401 |
| 5,049,377 | * | 9/1991 | Lamb et al. ............... 424/70 |
| 5,064,441 | * | 11/1991 | Kawase et al. ............... 8/405 |
| 5,102,655 | * | 4/1992 | Yoshirhara et al. ............... 424/62 |
| 5,130,124 | * | 7/1992 | Merianos et al. ............... 424/53 |
| 5,221,286 | * | 6/1993 | Singleton et al. ............... 8/406 |
| 5,328,685 | | 7/1994 | Janchitraponvej et al. . |
| 5,556,615 | * | 9/1996 | Janchitraponvej et al. ...... 424/70.11 |
| 5,560,750 | * | 10/1996 | Crews et al. ............... 8/431 |
| 5,730,966 | * | 3/1998 | Torgerson et al. ............... 424/70.11 |

FOREIGN PATENT DOCUMENTS

| | | |
|---|---|---|
| 3421358 | 12/1984 | (DE) . |
| 0218931 | 4/1987 | (EP) . |
| 0356665 | 8/1988 | (EP) . |
| 437075 | 7/1991 | (EP) . |
| 0829257 | 3/1998 | (EP) . |
| 2170830 | 8/1986 | (GB) . |
| 62/222585 | 9/1987 | (JP) . |
| 93/14024 | 7/1993 | (WO) . |

OTHER PUBLICATIONS

International Search Report Application No. PCt/EP 99/06097 mailed Jan. 26, 2000.

XP 002, 127, 088 & JP 09 227,347 (Chemical Abstract vol. 127, No. 16)(10/97) Abstract No. 225090 assigned to Kao Corp.

* cited by examiner

Primary Examiner—Thurman K. Page
Assistant Examiner—P. E. McQueeney
(74) Attorney, Agent, or Firm—Matthew Boxer

(57) ABSTRACT

There is described a conditioning composition for conditioning, lightening and highlighting hair which comprises:

(i) a peroxygen compound; and (ii) a conditioning agent, said composition having a pH of 5 or less. There is also described a method for conditioning lightening and highlighting hair which comprises treating said hair with a composition of the invention.

7 Claims, No Drawings

COMPOSITION FOR LIGHTENING AND HIGHLIGHTING HAIR

FIELD OF THE INVENTION

The present invention is directed to a conditioning composition which is also for lightening and/or highlighting hair.

BACKGROUND OF THE INVENTION AND PRIOR ART

It is known within the art to lighten and highlight hair with a peroxygen compound such as hydrogen peroxide. An object of the present invention, is to provide conditioners which contain stable peroxygen compounds and thus can be used as hair lighteners and highlighters as well as conditioners.

Current products on the market for lightening hair come in two forms. The first is a spray leave-on peroxide solution. This product is used occasionally when the hair will be exposed to sunlight after application. Examples of such products include Super Sun-In®, Super With Lemon Sun-In®, and Gradual Sun-In For Men®. Super Sun-In® has about 1.9% hydrogen peroxide at a pH of about 4.0. Super With Lemon Sun-In® has about 3.7% hydrogen peroxide at a pH of about 4.0. Gradual Sun-In For Men® has about 3.7% hydrogen peroxide at a pH of about 3.

The second product for lightening hair is a system which has two components: a bleaching component such as hydrogen peroxide and another component which is a bleach oil. This system requires two containers and/or two bottles, one for each of the components. These products will lighten and highlight the hair, however, often the result is damage that leaves hair in a less than healthy state.

It is known to prepare an unstable composition by combining a bleach with a shampoo or conditioner and immediately thereafter applying the resulting composition to the hair. This is usually done in a hair salon and will result in the immediate lightening of the hair. By contrast, stable conditioner compositions which gradually lighten and highlight the hair and which can easily be used at home are provided by the present invention.

Other publications which relate to the bleaching of hair are as follows:

WO 93/14024 A1 (1993);
JP 87/222585 (1987);
U.S. Pat. No. 4,656,043 (1987);
GB 86103053 (1986);
DE 84/3421358 (1984); and
EP 437,075 A (1990).

SUMMARY OF THE INVENTION

The invention relates to a conditioning composition for lightening and highlighting hair which comprises:

(i) a peroxygen compound; and
(ii) a conditioner vehicle which is stable in acid,
said composition having a pH less than 5.

The invention is also directed to a method for lightening and highlighting hair which comprises administering to the hair a lightening and highlighting effective amount of a composition comprising:

(i) a peroxygen compound
(ii) and a conditioner vehicle which is stable in acid
at a pH of less than 5, preferably about 2–4.5 and then rinsing said composition from the hair.

The peroxygen compound makes the conditioner composition a lightening and hair highlighting composition. Peroxygen compounds are not stable in conditioners at pH's of 5 and above. The composition is made acidic by addition of a acid, such as a mineral acid, like phosphoric acid or sulfuric acid. However, peroxygen compounds can go into conditioners provided that the pH is low enough.

Prior to the present invention, when peroxygen compounds were used to lighten hair, they were often used in bleach oils, or hair coloring compositions.

DETAILED DESCRIPTION OF THE INVENTION

There are two methods to lighten and highlight hair. The first method is to deposit onto the hair, molecules which color the hair. The second method is to bleach the natural pigment found in the hair. The present invention relates to the latter method.

Hair contains a number of different pigments, principally brown and red. When hair is bleached by chemicals or the sun, the brown pigments react faster, and therefore disappear faster than the red pigments. The change in the red to brown ratio changes the appearance of the hair giving more red shading to the natural color of the hair. This results in the lightening of the hair. The red color that appears is perceived as highlighting of the hair.

Peroxygen compounds have been used to bleach human hair. A preferred peroxygen compound is hydrogen peroxide. Hydrogen peroxide is stable, but will decompose under the appropriate conditions to form water and an active species of oxygen. The active species of oxygen is very reactive. It attacks and decolorizes the hair pigment.

It has surprisingly been found that a peroxygen compound, preferably hydrogen peroxide, is stable in a conditioner composition when present in about a 0.01 wt. % to about 10 wt. % (preferably 2%).

Use of conditioner compositions which have pH's of 5 or below stabilizes the peroxygen compound (which can be hydrogen peroxide) which is included in said compositions.

In the compositions of the present invention, any acid that can result in a pH of 5 or less may be employed. More specifically, any acid which has a pK such that it can be used to obtain a composition with a pH of 5 or less, may be employed. Exemplary of such acids are any mineral acid such as sulfuric acid or phosphoric acid. Appropriate organic acids such as citric acid may also be used.

As indicated above, the peroxide of the compositions of the invention can be employed with any conditioner, as long as the pH is low enough.

A conditioner agent stable to acid hydrolysis, such as a silicone compound having at least one quaternary ammonium moiety along with an ethoxylated monoquat is included in the conditioner. A clear conditioning composition of the present invention comprises: a clear conditioning composition comprising a silicone compound having at least one quaternary ammonium moiety, such as a diquaternary polydimethylsiloxane, and ethoxylated monoalkyl quat. The easy-to-apply, clear conditioning composition imparts excellent wet comb and dry comb properties to the hair, and the hair demonstrates improved physical and cosmetic properties, such as gloss, thickness, softness, manageability, body and less coating.

Clear conditioning agents may also include an amidoamine salt comprising an amidoamine compound having the chemical structure of formula I or II as shown below.

$$R_1\text{---}C(O)\text{---}NHR_2\text{---}N(R_3)R_4 \qquad \text{I}$$

or $$R_1\text{---}C(O)\text{---}NHR_2\text{---}Y \qquad \text{II}$$

or a mixture thereof, wherein $R_1$, is a fatty acid chain containing from about 11 to about 21 carbon atoms; $R_2$ is an alkylene group containing from about 2 to about 4 carbon atoms; $R_3$ is hydrogen, a methyl group, an ethyl group, or a hydroxyalkylene group containing from one to about 3 carbon atoms; $R_4$ is a methyl group, an ethyl group or a hydroxyalkylene group containing from one to about three carbon atoms; and Y is an organic heterocyclic nitrogen-containing moiety, and a sufficient amount of a suitable acid to neutralize the amidoamine compound.

These salts are described in U.S. Pat. No. 5,328,685 to Janchitraponvej et al, which is hereby incorporated by reference.

Conditioning compositions of the present invention also include compositions which are not clear.

In addition to the above-described essential ingredients, other common cosmetic components and additives can be incorporated in the conditioning composition with the essential ingredients, as long as the basic properties of the composition, and an ability to condition the hair, are not adversely affected. Such optional ingredients include, but are not limited to, humectants, inorganic salts, fragrances, dyes, hair colorants, hydrotropes, preservatives, water softening agents, acids, bases, buffers and the like. Optional components usually are present in weight percentages of less than about 2% each, and from about 5% to about 10% by weight of the composition in total.

Other optional ingredients can be included in the conditioning composition to enhance the ability of the composition to condition the hair. For example, other quaternary ammonium compounds can be included in the conditioning composition. A quaternary ammonium compound useful in the composition of the present invention preferably is a water-soluble quaternary ammonium compound having one or two long chain alkyl groups containing from about 8 to about 18 carbon atoms. The long chain alkyl groups also can include, in addition to, or as a substitute for, carbon and hydrogen atoms, ether linkages or similar water-solubilizing linkages. The remaining two to three substitutes of the quaternary nitrogen of the quaternary ammonium compound can be hydrogen; or benzyl; or short chain alkyl or hydroxyalkyl groups such as methyl, ethyl, hydroxymethyl or hydroxyethyl groups; or mixtures thereof, either of the same or of different identity. However, an oil-soluble, water dispersible quaternary ammonium compound, either alone or in combination with a water-soluble quaternary ammonium compound, also can be used in the composition of the present invention.

An optional thickener also can be included in the clear or opaque conditioning composition to improve composition esthetics and facilitate application of the composition to the hair. Nonionic thickeners in an amount of 0% to about 3% by weight are preferred. Exemplary thickeners are methylcellulose, hydroxybutyl methylcellulose, hydroxypropylcellulose, hydroxypropyl methylcellulose, hydroxyethyl ethylcellulose and hydroxyethylcellulose, di(hydrogenated tallow)phthalic acid amide, crosslinked maleic anhydride-methyl vinyl ether copolymer, guar gum, xanthan gum and gum arabic.

The carrier of the conditioning composition is predominantly water, but organic solvents also can be included in order to facilitate manufacturing of the composition or to provide esthetic properties, such as viscosity control. Suitable solvents include the lower alcohols like ethyl alcohol and isopropyl alcohol; glycol ethers, like 2-butoxyethanol, ethylene glycol monoethyl ether, propylene glycol and diethylene glycol monoethyl ether or monomethyl ether; and mixtures thereof. Non-aqueous solvents can be present in the conditioning composition of the present invention in an amount of about 1% to about 50%, and in particular about 5% to about 25%, by weight of the total weight of the carrier in the composition.

A composition of the present invention can be a composition that is stable to phase or ingredient separation at a temperature of about 25° C. for an indefinite period of time. For example, a clear conditioning composition of the present invention has demonstrated sufficient stability to phase and ingredient separation at temperatures normally found in commercial product storage and shipping to remain unaffected for periods of one year or more.

Non-limiting conditioning agents which may be used in opaque conditioners include:

stearyltrimethylammonium chloride;
behenetrimethylammonium chloride;
cetrimonium bromide;
soytrimonium chloride;
tallowtrimonium chloride;
dihyrogenatedtallowdimethylammonium chloride;
behentrimethylammonium methosulfate;
Peg-2 Oleammonium chloride;
dihyrogenatedtallowdimethylammonium bromide;
dihyrogenatedtallowdimethylammonium methosulfate;
palmityltrimethylammonium chloride;
hydrogenated tallowtrimethylammonium chloride;
hydrogenated tallowtrimethylammonium bromide;
dicetyidimethylammonium chloride;
distearyldimethylammonium chloride;
dipalmityidimethylammonium chloride;
hydrogenated tallowtrimethylammonium methosulfate;
cetrimonium tosylate:
eicosyltrimethylammonium chloride, and
ditallowdimethylammonium chloride.

Materials that can be used to opacify compositions of the invention include fatty esters, opacifying polymers, such as styrene polymers, like OPACIFIER 653 from Morton, International, Inc.; and fatty alcohols. The following is a non-limiting list of fatty alcohols.

cetyl alcohol;
stearyl alcohol;
cetearyl alcohol;
behenyl alcohol; and
arachidyl alcohol.

Conditioning compositions of the invention which are not clear also can include Lexamine S-13, dicetylammonium chloride, and ceteareth-20.

Lightening and/or highlighting the hair with the compositions of the invention is carried out by conditioning the hair, that is, (1) applying water to said hair (or starting the process with hair that is damp because it has already been shampooed); (2) applying to said hair a lightening and highlighting effective amount of a conditioning composition of the invention; (3) rubbing said hair with the hands or a hair appliance such as a comb; and (4) rinsing said hair with water. Each application of a composition of the invention results in a small degree of lightening and/or highlighting of the hair. By using a composition of the invention on a daily basis, the hair can be gradually lightened and highlighted until it reaches the desired state. At that point, conditioning with a composition of the invention is ceased, and hair of the desired color has been obtained until it grows out.

A person who used the conditioner compositions of the invention and also spends time in the sunlight may achieve hair lightening and/or hair highlighting more quickly than someone who uses the compositions of the invention but does not spend time in the sunlight. This is due to the additive effects of the bleaching of hair by sunlight and the chemical action of the conditioning compositions of the invention.

It will also be appreciated that the compositions of the invention have the advantage of enabling the user to obtain just the degree of highlighting and/or lightening that he or she desires at which point conditioning of the hair with the compositions of the invention is stopped, and this desired hair coloring will remain until the hair grows out.

Usually, some lightening or highlighting of the hair will be noticeable within the first ten to fourteen consecutive days of conditioning with a composition of the invention. Often, a composition of the invention will be used for up to about thirty consecutive days. However, as mentioned above, an advantage of the invention, is that a composition of the invention may be employed for more or less consecutive days than listed above, as desired by the user. In addition, the conditioning compositions may be employed every other day, or at even greater intervals as desired. If compositions of the invention are not employed on consecutive days, use may be made of the consumer's customary non-bleaching conditioner on the days when the bleaching conditioner of the invention is not being used. Moreover, after being applied, the conditioner may be left in the hair for a few seconds, or thirty seconds, or as long as 15 minutes. The longer the conditioner is left in the hair, the more the hair will be hilighted or lightened for a given application.

It will also be appreciated that the conditioning compositions of the invention also have the benefit of conditioning the hair at the same time as lightening or highlighting the hair. The conditioning compositions of the invention also have acceptable sensory qualities.

Compositions of the invention were used as conditioners and were evaluated by a trained panel of observers and found to lighten and highlight hair.

General Procedure for Preparing Conditioning Compositions of the Invention

Materials and chemicals used in the preparation of the compositions of the invention are either known or can be prepared according to known methods. A list of the components of compositions of the invention is as follows:

the solvent carrier is water wherein said water is substantially deionized;

conditioning agents and conditioning polymers are, for example;

Polyquaternium-10, and the like. Mixtures of the above polymers may also be employed;

the viscosity agent may be lauryl alcohol, sodium chloride, or ammonium chloride;

opacifiers selected from the group consisting of ethylene glycol monostearate and ethylene glycol distearate or mixtures thereof may optionally be employed;

a conditioning agent which is stable under low pH conditions, such as lauramine oxide may be employed, or an amidoamine such as isostearamidopropylmorpholine lactate may be employed;

a mineral acid such as phosphoric acid or sulfuric acid is employed;

a humectant such as propylene glycol may be employed;

a fragrance stable at low pH may be employed. Other cosmetic additives may be employed as well;

a thickener which may be used in the compositions of the invention can, for example, be selected from the group consisting of hydroxyethylcellulose, propylene glycol hydroxystearate, and alkanolamides. Preferably hydroxyethylcellulose (Natrosol) is used;

conditioners which may also be used are stearamidopropyl dimethylamine, Quaternium 80, or cetrimonium chloride;

A fatty alcohol selected from the group consisting of cetyl alcohol; stearyl alcohol; cetearyl alcohol; behenyl alcohol; and arachidyl alcohol;

a colorant which may be used in compositions of the invention is a dye like FD&C Blue #1;

a preservative which may be used in compositions of the invention is, for example, selected from such as Kathon CG from Rohm & Haas, and DMDM Hydantoin;

a peroxygen compound such as bromates, perborates or hydrogen peroxide may be used;

conditioner oils such as cyclomethicone and dimethicone;

solubilizers.

Materials from the above list are known or may be prepared according to known methods. A general description of the preparation of the compositions of the invention is set forth just below.

Compositions of the Invention are Prepared as Follows

Step 1. The solvent carrier, water, is added to a suitably sized tank;

Step 2. Moderate agitation is begun;

Step 3. Conditioning Polymers, such as Polyquaternium-10 are added and mixed until dissolved;

Step 4. Acid such as phosphoric acid or sulfuric acid, added and mixed until dissolved and the batch is at uniform pH;

Step 5. Any and all cosmetic additives are added;

Step 6. Hydrogen peroxide is added and mixed until the batch is uniform.

The above six steps can be done at from about room temperature to about a temperature above the melting point of the additives.

Compositions of the invention have ingredients which can fall within the following ranges:

| Ingredient | Amount in Wt % |
| --- | --- |
| conditioner | 0.01–10 |
| $H_2O_2$ | 0.01–10 |
| Acid | to provide a pH of 5 or less |
| Water | q.s. |

The following example shows a composition of the invention. This example is illustrative of compositions of the invention; however, the invention is not limited by this example.

Example 1

| Item # | Description | Wt. % |
|---|---|---|
| 1 | Water, Deionized | q.s. |
| 2 | Hydroxyethyl cellulose | 1.30 |
| 3 | PEG-2 Oleammonium Chloride (69%) & Propylene Gycol (31%) | 2.50 |
| 4 | Propylene Glycol, USP | 1.50 |
| 5 | Cetrimonium Chloride (30%) | 2.00 |
| 6 | Liquid Citric Acid 50% | 1.00 |
| 7 | Quaternium-80, 50% | 2.00 |
| 8 | FD&C Blue #1 (1%) | 0.05 |
| 9 | Disodium EDTA | 0.10 |
| 10 | Kathon CG from Rohm & Haas | 0.05 |
| 11 | DMDM Hydantoin | 0.10 |
| 12 | Fragrance | 0.40 |
| 13 | PEG-15 Nonyl Phenyl Ether (Polysorbate 20) | 0.40 |
| 14 | Hydrogen Peroxide, 35% CG | 4.00 |

A composition of the invention was prepared using the above materials and carrying out the following steps.

1. Water was added to a suitably-sized tank, and agitation was begun.
2. Hydroxyethyl cellulose was added and the mixture was heated to 125° F. Agitation was continued until the mixture was free of lumps and clear.
3. A mixture of PEG 2 and propylene glycol were added.
4. Propylene glycol, Cetrimonium chloride, Liquid citric acid, Quaternium-80, FD&C Blue #1 were added in the order listed.
5. Disodium EDTA in hot soft water was then added and mixed.
6. The mixture was then allowed to cool. When it reached 110° F. Kathon CG from Rohm & Haas and DMDM Hydantoin were added.
7. In a separate container were mixed fragrance and PEG-15 Nonyl Phenyl Ether (Polysorbate 20), until a clear solution was achieved. The clear solution was added to the main mixture, which was further cooled to 80° F. and mixed until uniform.
8. When the pH of the batch was 4.5 or below hydrogen peroxide was added and the resulting solution was mixed well.

The resulting mixture was a composition of the invention.

The above composition of the invention has passed stability tests in a three month study at 35° F., room temperature, and 110° F. These tests checked the compositions for color, odor, appearance, pH, viscosity, and the level of hydrogen peroxide. In a similar manner Examples 2 through 5 of the invention were prepared.

EXAMPLES 2–5

| Ingredient (As Is) | Ex. 2 | Ex. 3 | Ex. 4 | Ex. 5 |
|---|---|---|---|---|
| Deionized H20 | Q.S. | Q.S. | Q.S. | Q.S. |
| Hydroxyethyl cellulose | 1.3 | 1.3 | — | — |
| PEG-2 Oleammonium Cl & Propylene Glycol | 2.5 | 2.5 | — | — |
| Propylene Glycol | — | — | .5 | .5 |
| Stearamidopropyl dimethylamine | — | — | .5 | .5 |
| Dicetyldimonium Cl | — | — | 2.1 | 2.1 |
| Cetrimonium Cl vice versa for opaque | 2 | 2 | — | — |
| Quaternium-80 | 2 | 2 | — | — |
| Stearyl Alcohol & Ceteareth-20 | — | — | 1 | 1 |
| Cetyl Alcohol | — | — | 3.5 | 3.5 |
| Potassium Cl | — | — | .2 | .2 |
| Dosodium, EDTA | .1 | .1 | .1 | .1 |
| Kathon CG from Rohm & Haas | .05 | .05 | .08 | .08 |
| DMDM Hydantoin | .1 | .1 | .1 | .1 |
| Cyclomethicone | — | — | 1.8 | 1.8 |
| Dimethicone | — | .1 | .1 | |
| Fragrance | .4 | .4 | .4 | .4 |
| PEG-15 Nonyl Phenyl Ether | .4 | .4 | — | — |
| Liquid Citric Acid, 50% | .085 | .1 | .685 | .185 |
| Phosphoric Acid, 85% | — | — | — | .1 |
| Hydrogen Peroxide, 35% CG | 4 | 4 | 4 | 11.45 |

The studies which are given below show the advantageous properties of the compositions of the invention.

Instron Wet Combing and Static Charge Build-up Studies

The Instron combing test and combing force are as described in Garcia et al, J. Soc. Cosmet. Chem. 27:379 (1976) which is hereby incorporated by reference. Static charge test methods and the definition of static charge are as described in Lunn et al., J. Soc. Cosmet. Chem. 28:549 (1977) which is hereby incorporated by reference.

| Ingredients | Composition A | Composition B |
|---|---|---|
| Deionized Water | Q.S. | Q.S. |
| Hydroxyethyl cellulose | 1.3 | 1.3 |
| PEG-2 Oleammonium Chloride (69% active) & Propylene Glycol (31% active) | 2.5 | 2.5 |
| Propylene Glycol, USP | 1.5 | 1.5 |
| Cetrimonium Chloride, 30% active | 2 | 2 |
| Quaternium-80, 50% active | 2 | 2 |
| FD&C Blue #1, 85% active | .00003 | .0005 |
| Disodium EDTA | .1 | .1 |
| Kathon CG from Rohm & Haas | .05 | .05 |
| DMDM Hydantoin | .1 | .1 |
| Benzophenone-4 | .05 | — |
| Fragrance | .4 | .4 |
| PEG-15 Nonyl Phenyl Ether | .4 | .4 |
| Liquid Citric Acid, 50% active | .07 | .1 |
| Hydrogen Peroxide, 35% active | — | 4 |
| Combing Force (g force) No significant difference found | 10.2 | 8.4 |
| Absolute Static Build-up (kV/m) No significant difference found | 12.6 | 9.6 |

As shown in the above table, addition of Hydrogen Peroxide does not damage the hair, that is, it does not decrease the ease of Wet Combing or increase Static Charge Build-up).

Trained Panel Evaluation of Tresses Treated 1× and 5× with Composition B

Experimental Procedure

Two (2) Virgin Brown Tresses from DeMeo Bros., New York, were shampooed with a Clarifying Shampoo, rinsed then dried. The 1st Tress, Tress 1 was shampooed, rinsed then dried. The 2nd Tress, Tress 2 was shampooed, rinsed, then treated with 5 cc of composition B. Composition B was spread through the tress and allowed to remain on the hair for 3 minutes, then rinsed and dried. Tress 1 and Tress 2 were evaluated together to determine if their was any lightening in Tress 2 (evaluation by trained panel of five). Tress 2 was then shampooed, rinsed, and treated with composition B for 3 minutes, rinsed then dried 4 times. Tress 2 was again evaluated versus Tress 1 by trained panel.

| Ingredients | Composition B |
| --- | --- |
| Deionized Water | Q.S. |
| Hydroxyethyl cellulose | 1.3 |
| PEG-2 Olealmonium Chloride (69% active) & Propylene Glycol (31% active) | 2.5 |
| Propylene Glycol, USP | 1.5 |
| Cetrimonium Chloride, 30% active | 2 |
| Quaternium-80, 50% active | 2 |
| FD&C Blue #1, 85% active | .0005 |
| Disodium EDTA | .1 |
| Kathon CG from Rohm & Haas | .05 |
| DMDM Hydantoin | .1 |
| Fragrance | .4 |
| PEG-15 Nonyl Phenyl Ether | .4 |
| Liquid Citric Acid, 50% active | .1 |
| Hydrogen Peroxide, 35% active | 4 |
| # of Trained Panel who saw lightening of tress 2 versus tress 1 after 1x treatment | 1 |
| # of Trained Panel who saw lightening of tress 2 versus tress 1 after 5x treatment | 6 |

Modifications and variations of the invention as set forth above, can be made without departing from the spirit and the scope thereof.

What is claimed is:

1. A composition for conditioning, lightening and highlighting hair comprising:

(i) a peroxygen compound; and (ii) a conditioning agent, wherein the conditioning agent is a silicone compound having at least one quaternary ammonium moiety and an ethoxylated monoalky quat;

said composition having a pH of 5 or less.

2. A composition according to claim 1, wherein the conditioning agent is a diquaternary polydimethylsiloxane and an ethoxylated monoalkyl quat.

3. A composition according to claim 1, which is clear.

4. A composition according to claim 3, comprising a clear conditioning agent which is an amidoamine salt wherein the amidoamine salt comprises: an amidoamine compound having a chemical structure of formula I or II

or

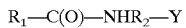

or a mixture thereof, wherein $R_1$ is a fatty acid chain contain or a mixture thereof, wherein $R_1$ is a fatty acid chain containing from about 11 to about 21 carbon atoms; $R_2$ is an alkylene group containing from about 2 to about 4 carbon atoms; $R_3$ is hydrogen, a methyl group, an ethyl group, or a hydroxyalkylene group containing from one to about 3 carbon atoms; $R_4$ is a methyl group, an ethyl group or a hydroxyalkylene group containing from one to about three carbon atoms; and Y is an organic heterocyclic nitrogen-containing moiety, and a sufficient amount of a suitable acid to neutralize the amidoamine compound.

5. A composition according to claim 3, comprising a clear conditioning agent which is PEG-2 Oleammonium chloride & propylene glycol.

6. A composition according to claim 1, which further comprises lauryltrimethylammonium chloride, stearyltri(2-hydroxyethyl)ammonium chloride, lauryidimethylbenzylammonium chloride, oleyidimethylbenzylammonium chloride, dilauryidimethylammonium chloride, cetyidimethylbenzylammonium chloride, dicetyidimethylammonium chloride, laurylpyridinium chloride, and cetylpyridinium chloride.

7. A composition according to claim 1, which further comprises a nonionic thickener selected from the group consisting of methylcellulose, hydroxybutyl methylcellulose, hydroxypropylcellulose, hydroxypropyl methylcellulose, hydroxyethyl ethylcellulose and hydroxyethylcellulose, di(hydrogenated tallow)phthalic acid amide, crosslinked maleic anhydride-methyl vinyl ether copolymer, guar gum, xanthan gum and gum arabic.

* * * * *